(12) United States Patent
Ratnamohan et al.

(10) Patent No.: US 6,627,418 B1
(45) Date of Patent: Sep. 30, 2003

(54) DETECTION OF HUMAN HERPES VIRUS 6 (HHV6)

(75) Inventors: Vigneswary Mala Ratnamohan, Carlingford (AU); Anthony Lawrence Cunningham, Cheltenham (AU)

(73) Assignee: Westmead Institute of Health Research (AU)

( * ) Notice: Subject to any disclaimer, the term of this patent is extended or adjusted under 35 U.S.C. 154(b) by 0 days.

(21) Appl. No.: 09/787,628

(22) PCT Filed: Sep. 21, 1999

(86) PCT No.: PCT/AU99/00806
§ 371 (c)(1),
(2), (4) Date: May 15, 2001

(87) PCT Pub. No.: WO00/17219
PCT Pub. Date: Mar. 30, 2000

(30) Foreign Application Priority Data

Sep. 21, 1998 (AU) .............................................. PP6052

(51) Int. Cl.[7] .......................... C12P 19/34; A61K 39/12
(52) U.S. Cl. .................. 435/91.1; 435/91.2; 435/91.33; 424/204.1; 536/23.72
(58) Field of Search ........................... 536/24.33, 23.72; 424/204.1; 435/91.2, 91.33, 91.1

(56) References Cited

U.S. PATENT DOCUMENTS 5,545,520 A * 8/1996 Collandre et al. ............. 435/5

OTHER PUBLICATIONS

Lawrence et al, "Human herpesvirus 6 (strain U1102) encodes homologues," Journal of General Virology, vol. 76, pp. 147–152 (1995).

Lawrence et al, "Human herpesvirus 6 Is Closely Related to Human Cytomegalovirus," Journal of Virology, Jan. 1990, pp. 287–299.

Pellett et al, "A Strongly Immunogreactive Viron Protein . . . ," Virology, vol. 195, pp. 521–531 (1993).

* cited by examiner

Primary Examiner—Ali R. Salimi
(74) Attorney, Agent, or Firm—Nixon & Vanderhye

(57) ABSTRACT

The present invention relates to methods for detecting viral pathogens, particularly human herpes virus S (HHV6), preferably using polymerase chain reaction (PCR) techniques. Primer sequences useful in these methods are also described. In a first aspect, the invention provides an isolated nucleic add molecule complementary to and specific for human herpes virus 6 (HHV6) DNA including a sequence selected from 5'CTTCTGTTTTAAGTCGTACAGGAGT (SEQ ID NO: 1), 5'ACAATTGCCATTTCGGGGAAGTAC (SEQ ID NO: 2), and functionally equivalent sequences. A method for detecting HHV6 in a sample suspected of containing HHV6 is also provided.

3 Claims, 2 Drawing Sheets

# DETECTION OF HUMAN HERPES VIRUS 6 (HHV6)

TECHNICAL FIELD

The present invention relates to methods for detecting viral pathogens, particularly human herpes virus 6 (HHV6), using polymerase chain reaction (PCR) techniques.

BACKGROUND ART

Cytomegalovirus (CMV) shedding and disease are classically associated with immunosuppressive therapy following organ transplantation in two distinct settings. Primary disease, often with organ involvement usually occurs within the first 6 weeks. The less severe secondary disease, two to three months after transplantation may be caused by reactivation or reinfection with CMV. Biological anti-rejection therapy, however, including OKT3 and anti-thymocyte globulins (ATG), is now the major risk factor for CMV disease in the CMV seropositive patient.

Other herpesviruses, including human herpes virus 6 (HHV6), reactivate during periods of intense immunosuppression. Infection with HHV6 is usual in the first one to three years of life and a minority develop exanthem subitum during primary infection. HHV6 antibody levels tend to decrease in adults over 30 years of age and may reach undetectable levels. Two major subspecies of HHV6, variants A and B, have been distinguished on genetic, antigenic and biological characteristics. Reactivation of HHV6 (variant B) has been reported in bone marrow, renal and liver transplant patients and has been associated with hepatitis, severe interstitial pneumonitis and encephalitis. Serologic evidence has been reported for simultaneous reactivation of CMV and HHV6 after renal transplantation and there have been reports of dual infection with CMV and either HHV6 or HHV7 in transplant patients. Prospective studies of the role of HHV6 in febrile disease following renal transplantation and the potential interaction between CMV and HHV6 reactivation in causing disease are lacking.

Viral markers which can accurately predict CMV/HHV6 disease, the need for antiviral therapy, and likelihood of successful response in renal transplant recipients is an important clinical priority. Buffy coat cultures have been a more reliable predictor of CMV disease in renal transplantation than detection in urine. More recently, detection of CMV DNA in plasma or quantification in urine or buffy coat have been shown to be predictive of disease in liver, renal transplant or HIV infected patients. HHV6 DNA has been detected in sera from immunosuppressed patients with HIV infection or undergoing bone marrow transplantation. The present inventors have examined prospectively reactivation or infection with CMV and HHV6 detected as viral DNA by polymerase chain reaction (PCR) in serum and urine, to determine the relative contributions of the two viruses towards disease during renal transplantation and to consider whether active infection of both viruses together may predict either the frequency or severity of disease.

The present inventors have detected an association between viral infections and have developed new methods to detect and differentiate viral infections in organ transplant and immunocompromised patients.

DISCLOSURE OF INVENTION

In a first aspect, the present invention consists in an isolated nucleic acid molecule complementary to and specific for human herpes virus 6 (HHV6) DNA including a sequence selected from the group consisting of 5'CTTCT-GTTTTAAGTCGTACAGGAGT (SEQ ID NO: 1), 5'ACAAGTTGCCATTTCGGGGAAGTAC (SEQ ID NO: 2), and functionally equivalent sequences.

In a preferred embodiment of the present invention, the molecule consists of the sequence 5'CTTCTGTTT-TAAGTCGTACAGGAGT (SEQ ID NO: 1), 5'ACAAGT-TGCCATTTCGGGGAAGTAC (SEQ ID NO: 2), or a functional equivalent of either one of these sequences.

A functionally equivalent sequence is defined as a sequence being different by one or more bases but still specific for and able to bind to the DNA of HHV6.

In a second aspect, the present invention consists in a method for amplifying HHV6 DNA which method involves the use of a pair of oligonucleotide primers comprising the sequences 5'CTTCTGTTTTAAGTCGTACAGGAGT (SEQ ID NO: 1)and 5'ACAAGTTGCCATTTCGGGGAAGTAC (SEQ ID NO: 2), or including functionally equivalent sequences. Preferably, the primers consist of the sequences 5'CTTCTGTTTTAAGTCGTACAGGAGT (SEQ ID NO: 1)and 5'ACAAGTTGCCATTTCGGGGAAGTAC (SEQ ID NO: 2), or functionally equivalent sequences.

In a third aspect, the present invention consists in a method of detecting HHV6 in a sample containing HHV6, the method comprising the steps of:
 (a) optionally, amplifying viral DNA present in the sample by polymerase chain reaction techniques using outer primers complimentary to the viral DNA;
 (b) adding to the sample, or to the sample having undergone optional amplification step (a), a pair of inner oligonucleotide primers complementary to and specific for HHV6 DNA, wherein the inner primers include the sequences 5'AAGCTTGCACAATGCCAAAAAA-CAG (SEQ ID NO: 3) and 5'CTCGAGTATGC-CGAGACCCCTAATC (SEQ ID NO: 4), or functionally equivalent sequences;
 (c) carrying out polymerase chain reaction techniques on the sample so as to amplifying the HHV6 DNA spanned by the inner primers present in the sample; and
 (d) detecting the amplified HHV6 DNA.

In a preferred embodiment of the third aspect of the present invention, the method comprises the steps of:
 (a) optionally, amplifying viral DNA present in the sample by polymerase chain reaction techniques by
  (i) adding outer primers, complimentary to the viral DNA in the sample,
  (ii) providing buffers, reagents, nucleotides and a thermostable DNA polymerase to the sample to form a reaction mixture,
  (iii) heating the reaction mixture to a temperature such that double stranded viral DNA present denatures to form single stranded DNA molecules,
  (iv) cooling the reaction mixture to a temperature such that the outer primers anneal to their respective complementary sequences on the denatured single stranded DNA molecules,
  (v) heating the reaction mixture to a temperature such that the DNA polymerase extends the primers to form new double stranded DNA molecules spanning the region of DNA defined by the outer primers, and
  (vi) repeating steps (iii), (iv) and (v) such that the number of copies of the region of DNA encoding the double stranded viral DNA is amplified;
 (b) adding to the optionally amplified sample a pair of inner oligonucleotide primers complementary to and specific for HHV6 DNA, wherein the inner primers include the sequences 5'AAGCTTGCACAATGC-CAAAAAACAG (SEQ ID NO: 3)and 5'CTCGAG-TATGCCGAGACCCCTAATC (SEQ ID NO: 4), or functionally equivalent sequences;

(c) heating the reaction mixture to a temperature such that the optionally amplified double stranded viral DNA denatures to form single stranded DNA molecules;

(d) cooling the reaction mixture to a temperature such that the inner primers anneal to their respective complementary sequences on the denatured DNA;

(e) heating the reaction mixture to a temperature such that the DNA polymerase extends the primers to form new double stranded DNA molecules spanning the region of DNA defined by the inner primers;

(f) repeating steps (c), (d) and (e) such that the number of copies of the region of DNA is amplified; and (g) detecting the amplified DNA.

The sample can be any sample including fixed or frozen tissue samples, and any biological fluid including blood, serum, urine, semen, sputum, saliva, cerebrospinal spinal fluid, cord blood and other excretions. Preferably, the sample is serum or urine. The same can be pre-treated to extract or concentrate the nucleic acid material (DNA) from the sample by standard methods known in the art. Outer primers comprising the sequences 5'CTTCTGTTTTAAGTCGTA-CAGGAGT (SEQ ID NO: 1) and 5'ACAAGTTGC-CATTTCGGGGAAGTAC (SEQ ID NO: 2) have been found to be particularly suitable for the optional steps of amplifying viral DNA in the sample. More preferably, the outer primers consist of the sequences 5'CTTCTGTTT-TAAGTCGTACAGGAGT (SEQ ID NO: 3)and 5'ACAAGTTGCCATTTCGGGGAAGTAC (SEQ ID NO: 2).

Preferably, the inner primers consist of the sequences 5'CTTCTGTTTTAAGTCGTACAGGAGT (SEQ ID NO: 3)and 5'ACAAGTTGCCATTTCGGGGAAGTAC (SEQ ID NO: 4). It will be appreciated that other outer and inner primers based on the preferred primers according to the present invention and having slight differences in their sequences may also be suitable.

The detection of the amplified DNA in step (g) can be by any means known to the art. Preferably, the DNA is separated by electrophoresis and the DNA detected by a detectably-labelled viral specific probe. One such probe suitable includes the sequence 5'AACTGTCTGACTG-GCAAAAACTTTT (SEQ ID NO: 5).

The term "polymerase chain reaction" or "PCR" when used herein generally refers to a procedure where minute amounts of a specific piece of nucleic acid, RNA and/or DNA, are amplified as described in the literature (1,2). Generally, sequence information from the ends of the region of interest or beyond needs to be available, such that oligonucleotide primers can be designed; these primers will be identical in sequence or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage or plasmid sequences, etc (3,4).

As used herein, PCR is considered to be one, but not the only, example of a nucleic acid polymerase reaction method for amplifying a nucleic acid test sample, comprising the use of an established nucleic acid (DNA or RNA) as a primer, and utilises a nucleic acid polymerase to amplify or generate a specific piece of nucleic acid or to amplify or generate a specific piece of nucleic acid which is complementary to a particular nucleic acid (5,6).

The terms "ligation chain reaction" or "LCR" or "ligation amplification reaction" or "LAR" when used herein generally refer to a procedure where minute amounts of a specific piece of nucleic acid, RNA and/or DNA, are amplified (7,8). Generally, sequence information from the region of interest needs to be available, such that oligonucleotide pairs can be designed that are complementary to adjacent sites on an appropriate nucleic acid template. The oligonucleotide pair is ligated together by the action of a ligase enzyme. The amount of ligated product may be increased by either linear or exponential amplification using sequential rounds of such template-dependent ligation. In the case of linear amplification, a single pair of oligonucleotides is ligated, the reaction is heated to dissociate the ligation product from its template, and similar additional rounds of ligation are performed. Exponential amplification utilises two pairs of oligonucleotides, one pair being complementary to one strand of a target sequence and the other pair being complementary to the second strand of the target sequence. In this case the products of ligation serve as mutually complementary templates for subsequent rounds of ligation, interspersed with heating to separate the ligated products from the template strands. A single base-pair mismatch between the annealed oligonucleotides and the template prevents ligation, thus allowing the distinction of single base-pair differences between DNA templates.

LAR can be used to amplify specific RNA sequences, specific DNA sequences from total genomic DNA, and cDNA transcribed from total cellular RNA, bacteriophage or plasmid sequences, etc (7,8).

As used herein, LAR is considered to be one, but not the only, example of a nucleic acid ligase reaction method for amplifying a nucleic acid test sample, comprising the use of an established nucleic acid (DNA or RNA) as a primer/probe, and utilises a nucleic acid ligase to amplify or generate a specific piece of nucleic acid or to amplify or generate a specific piece of nucleic acid which is complementary to a particular nucleic acid (9,10).

As an example, PCR methods and conditions found to be particularly suitable for the third aspect of the present invention are set out below. Specimen DNA was amplified in a final volume of 100 $\mu$l of 10 mM Tris (pH 8.3), 50 mM KCI, 2.0 mM $MgCl_2$, (2.5 mM for CMV) 0.01% gelatin, 0.1% Tritonx100, 0.2 mM of dNTPs, 20 pmoles of each outer primer and 1.5 units of Taq DNA polymerase (Promega, Madison, USA). After an initial denaturation for 3 minutes at 94° C., the DNA was subjected to 30 cycles of amplification with 1 minute at 94° C., 40 seconds at 55° C. (60° C. for CMV) and 1.5 minutes at 72° C. followed by a final extension at 72° C. for 7 mins in thermal cycler. When nested PCR was performed for HHV6, 2 $\mu$l of the first product was transferred to a fresh tube containing similar concentrations of the reagents, except that the inner primers were used. Conditions of cycling were similar, but with 20 cycles for the primary amplification followed by 30 cycles for the nested. The amplified products were analysed by electrophoresis on an 8% polyacrylamide gel and hybridisation with a radiolabelled probe was carried out.

In a fourth aspect, the present invention consists in a method of detecting or diagnosing infection with HHV6 in a subject, the method including carrying out the method according to the third aspect of the present invention on a sample from the subject to detect the presence of HHV6 in the sample.

The present inventors have found that the method is particularly suitable for detecting the presence of HHV6 in organ transplant recipients and donors. It will be appreciated, however, that the method would be applicable for other uses where the detection or diagnosis of HHV6 is required.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

In order that the present invention may be more clearly understood, preferred forms will be described in the following examples with reference to the accompanying drawings.

MODES FOR CARRYING OUT THE INVENTION

Materials and Methods

Patients

Figure 1:
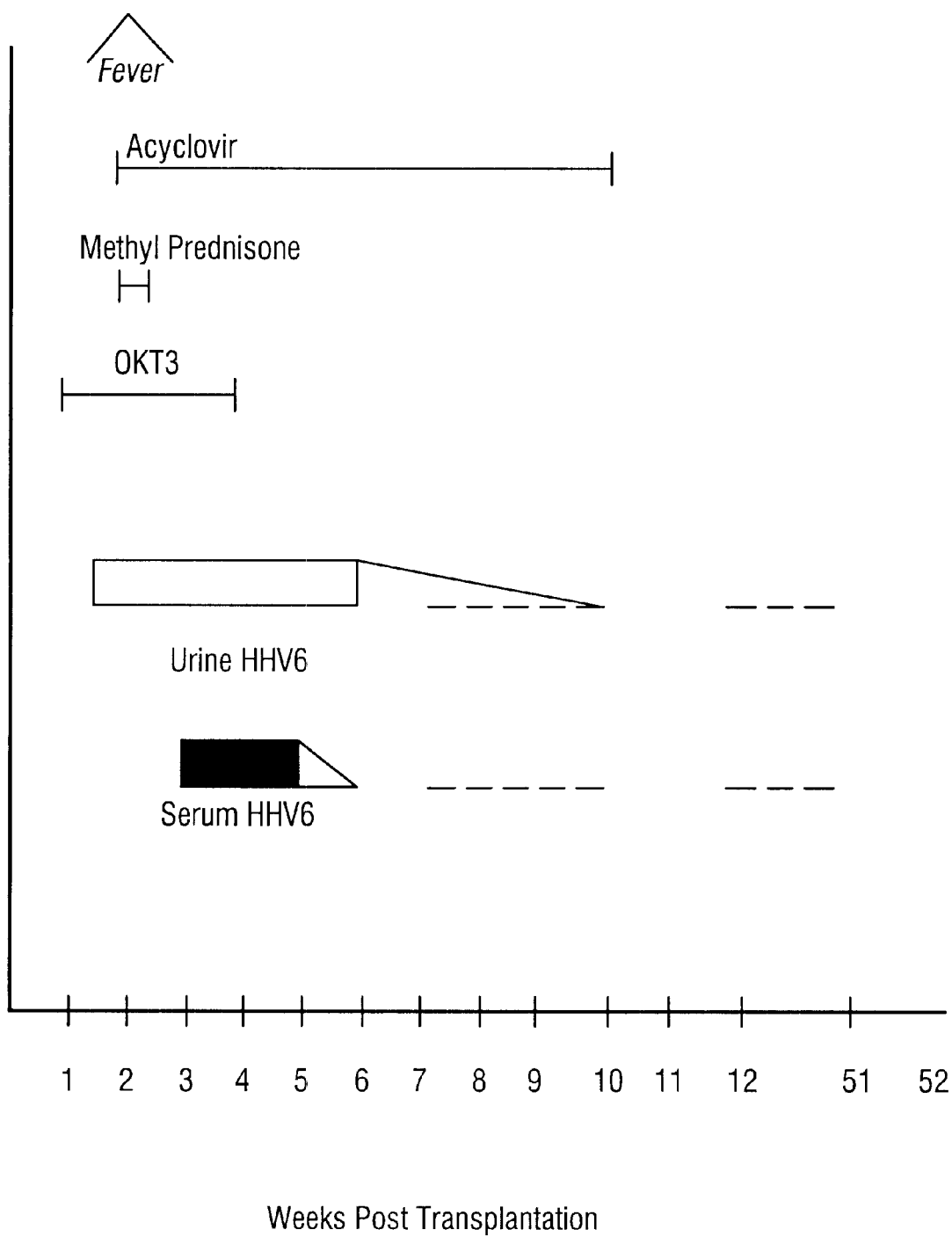
FIG. 1 shows febrile disease associated with HHV6 DNA shedding in urine and serum in a patient receiving OKT3 after renal transplantation. Note that urinary shedding of HHV6 commenced within a week of OKT3 and was followed by the onset of fever and by serum HHV6 shedding, during administration of oral acyclovir. Dashed lines show weeks when specimens were unable to be collected for CMV/HHV6 DNA.

Thirty consecutive recipients of renal (n=16) or renal-pancreas (n=14) transplants received an initial immunosuppressive regime of cyclosporine (10 mg/kg/day), azathioprine (1.5 mg/kg/day) and prednisolone (20 mg/day). Between one and seven weeks after transplantation, 10 patients received OKT3 (Orthoclone, Jansen Cilag) alone, eight received ATG (Fresenius, Germany) alone, four received both OKT3 and ATG and eight received neither OKT3 or ATG. OKT3 was used for the treatment of first acute rejection episodes in simultaneous renal pancreas transplants and either OKT3 or ATG were used for treatment of steroid resistant rejection of renal transplants.

Heparinised blood, clotted blood and urine were collected from the patients immediately before transplantation (day 0) and at 2, 6, 12 and 52 weeks post-transplantation. When patients were administered OKT3 or ATG, samples were taken before the first dose and for 3 consecutive weeks after OKT3/ATG. When any patient developed presumptive viral disease (vide infra), samples were collected at weekly intervals for 3 weeks.

Definition of Disease

The viral syndrome was defined prospectively as either of the following:

1) Fever (>38.5° C.) for at least 3 days which could not be explained by other organisms, drugs or toxins after careful investigation. In these patients either CMV or HHV6 DNA or both were always present in serum or urine.

2) Fever (>38.5° C.) for at least 3 days with at least one of the following: neutropaenia, abnormal liver function tests (especially elevated serum alanine aminotransferase and gamma glutamyltransferase) or invasive disease as proved by biopsy of the gastrointestinal tract or lung. CMV or HHV6 DNA or both were always present in the serum or urine.

Mild disease was defined as fever of short duration (3–7 days), moderate disease as fever of longer duration with neutropaenia and severe disease as fever, neutropaenia and tissue invasion (e.g. oesophagitis).

Polymerase Chain Reaction for Detection of CMV and HHV6 DNA

Primers and Probes

Sequences of primers and probes were derived from the U1102 strain (subtype A) of HHV6 (11,12) and the UL123 gene, exon 4 of CMV Towne Strain (13) (Table 1). The primers were initially checked in PCR reactions with EBV, CMV, HSV, VZV and HHV6 DNA to determine the specificity of the primers selected.

TABLE 1

Primer and probe sequences used in the detection of HHV6 and CMV DNA in serum and urine

HHV6

Inner primer pair location—17405–17627

(A) H6.6 5'AAGCTTGCACAATGCCAAAAAACAG (SEQ ID NO: 3)—inner primer (B) H6.7 5'CTCGAGTATGCCGAGACCCCTAATC (SEQ ID NO: 4)—inner primer Probe (C) H6.6/7 5'AACTGTCTGACTCGGCAAAAACTTTT (SEQ ID NO: 5)—probe Outer primer pair location 17728–17310

(D) H6.8 5'CTTCTGTTTTAAGTCGTACAGGAGT (SEQ ID NO: 1)—outer primer (E) H6.9 5'ACAAGTTGCCATTTCGGGGAAGTAC (SEQ ID NO: 2)—outer primer

CMV

Location 731–1165

MIE.4 5'CCAAGCGGCCTCTGATAACCAAGCC (SEQ ID NO: 6)—primer

MIE.5 5'CAGCACCATCCTCCTCTTCCTCTGG (SEQ ID NO: 7)—primer

MIE 5'AGGCTATTGTAGCCTACACTTTG (SEQ ID NO: 8)—probe

PCR was nested for the detection of HHV6 DNA in serum, the sequences of the outer primers were, D and E (Table 1) while oligos A and B were used as the inner primers and oligo C was end labelled and used as the probe after southern transfer.

Extraction of Viral DNA

Urine was concentrated with polyethylene glycol (8% W/V of PEG 6000, BDH Chemicals, Victoria, Australia) 14) and 5 µl was amplified in each PCR reaction.

Minced tissue from 2 mm$^3$ biopsy, cell pellets from 3×10$^6$ J.Jahn cells infected with HHV6 or human embryonic fibroblasts (HEF) infected with CMV were treated with 500 µl of lysis buffer (150 mM Tris-HCl-pH-8.0, 50 mM NaCl, 0.1% SDS, 50 µg proteinase K) at 55° C. for 2 hrs followed by heating to 95° C. for 5 mins and centrifuged at 14,000g for 5 mins. The supernatant was diluted to contain 3 pg to 30 fg of viral DNA (positive control) or 1 µg of test specimen DNA and used for PCR.

Serum DNA was precipitated from 200–300 µl of serum by standard phenol/ChCl₃ and re-suspended in 40 to 50 µl of distilled water. Five µl was used in each PCR reaction. Serum DNA extracted from nine healthy laboratory staff was also included in the study to determine whether cell-free HHV6 DNA was detectable in healthy individuals.

HHV6 and CMV PCR

Specimen DNA was amplified in a final volume of 100 µl of 10 mM Tris (pH 8.3), 50 mM KCI, 2.0 mM MgCl₂ (2.5 mM for CMV) 0.01% gelatin, 0.1% Tritonx100, 0.2 mM of dNTPs, 20 pmoles of each primer and 1.5 units of Taq DNA polymerase (Promega,Madison, USA). After an initial denaturation for 3 minutes at 94° C. the DNA was subjected to 30 cycles of amplification with 1 minute at 94° C., 40 seconds at 55° C. (60° C. for CMV) and 1.5 minutes at 72° C. followed by a final extension at 72° C. for 7 mins in a Perkin Elmer Cetus thermal cycler.

When nested PCR was performed for HHV6, 2 µl of the first product was transferred to a fresh tube containing similar concentrations of the reagents, except that the inner primers were used. Conditions of cycling were similar, but with 20 cycles for the primary amplification followed by 30 cycles for the nested.

The amplified products were analysed by electrophoresis on an 8% polyacrylamide gel and hybridisation with radio-labelled probe as described previously (14).

CMV Early Antigen Detection by Culture Immunofluorescence

CMV early antigen (EA) was detected in HEF by the shell vial method (14) using anti-human CMV monoclonal antibodies to the immediate early and early nuclear antigens (Syva, CA).

HHV6 and CMV Serology

HHV6 IgG and IgM titres were determined by the indirect fluorescent antibody method (IFA) on HHV6 infected J.Jahn cells (15). CMV serology was performed by the ELISA method (Medac, Hamburg, Germany).

Clinical Data Provision

Data provided to the clinical transplantation service included only that data specifically requested and only for CMV serology and CMV early antigen detection by culture Immunofluorescence. All other tests results were unavailable and were thus not used to guide clinical decision taking with respect to prophylactic, immunosuppressive or therapeutic measures. No HHV6 data were available at any time to the clinical service.

Statistics

The significance of associations between treatments, viral DNA in serum and urine and with disease and the relative independence of these parameters as predictors of disease were examined using logistic regression analysis and a best fitting multivariate model.

Results

Viral disease occurred in 15 patients (Table 2) and was severe in one who developed high fever, neutropaenia and oesophagitis with relapse after treatment with ganciclovir, moderate in 10, and mild self limiting pyrexia in the remaining 4, with disease being more frequent after administration of either OKT3 or ATG (13/22 compared with 2/8, p=0.048, Fishers Exact Test).

All five CMV seronegative recipients of CMV positive kidneys seroconverted for CMV and developed moderate (14) to severe (11) disease which was treated with ganciclovir. In addition to development of IgG antibodies to CMV all five developed specific IgM and also shed CMV DNA in the urine. The five patients, however, also shed HHV6 in their urine, simultaneously in four patients and delayed by one week in one. In the three serum specimens available (3/3) had both CMV and HHV6 DNA. HHV6 specific IgM was detected in the serum of four of the five. This suggested that all five patients developed combined CMV and HHV6 infection.

Three of four CMV seronegative recipients who were transplanted with CMV seronegative kidneys developed disease. They had not been given blood transfusions, no CMV DNA was detected and none became CMV IgG positive. All three patients with disease did however have HHV6 DNA detected in urine and serum, and demonstrated a specific IgM antibody response (one seroconverted for HHV6 IgG and one showed a four-fold rise in titre). HHV6 disease was characterised by moderate to high classical spiking fever lasting one to three weeks, with marked abnormalities of liver function tests including elevated serum alanine transaminase and gamma glutamyl transpeptidase, but without neutropaenia, or other organ involvement (see FIG. 1).

TABLE 2

Correlation of viral disease with CMV sero-status and with the presence of HHV6 and CMV DNA in urine and serum

| CMV Status pre-transplant | | | | Virus DNA detected in Urine (and Serum) | | | |
|---|---|---|---|---|---|---|---|
| Donor | Recipient | (n) | Viral Disease Status (n) | CMV | HHV6 | BOTH | NEITHER |
| Pos | Neg | (5) | Disease (5) | — | — | 5(*) | 0 |
| | | | No disease (0) | — | — | — | — |
| Neg | Neg | (4) | Disease (3) | 0 | 3 (3) | 0 | 0 |
| | | | No disease (1) | 0 | 0 | 0 | 1 |
| Pos or Neg | Pos | (21) | Disease (7) | 1(0) | 0 | 6(⁺) | 0 |
| | | | No disease (14) | 5(1) | 1(0) | 0 | 8 |
| Totals | | (30) | Disease (15) | 1(0) | 3(3) | 11(⁺⁺) | 0 |
| | | | No disease (15) | 5(1) | 1(0) | 0 | 9 |

*3 CMV, 3 HHV6 positive in 3 sera
⁺3 CMV, 1 HHV6 positive in 5 sera
⁺⁺6 CMV, 3 HHV6 positive in 8 sera Thirteen of the 21 CMV seropositive recipients received OKT3/ATG. Seven developed disease (five after use of OKT3/ATG), six of whom had both CMV and HHV6 DNA detected in urine (three had CMV DNA and one HHV6 DNA in serum, one serum being unavailable).

Shedding of CMV and HHV6 DNA in Serum and Urine

Rather than rely on the above classical paradigm for understanding the relationship between clinical disease and viral testing, the present inventors also reviewed the data considering detection of DNA and specific IgG and IgM responses to both viruses.

HHV6 DNA was not detectable in any transplant patient's sera after direct PCR using primers A and B (Table 1) or after one round of amplification with primers D and E. Nested PCR using D and E as primers followed by a second round of amplification with primers A and B was useful for the detection of HHV6 DNA in patient's sera. None of the sera from nine healthy donors or pre-transplant sera had detectable HHV6 DNA using the nested PCR.

Figure 2:
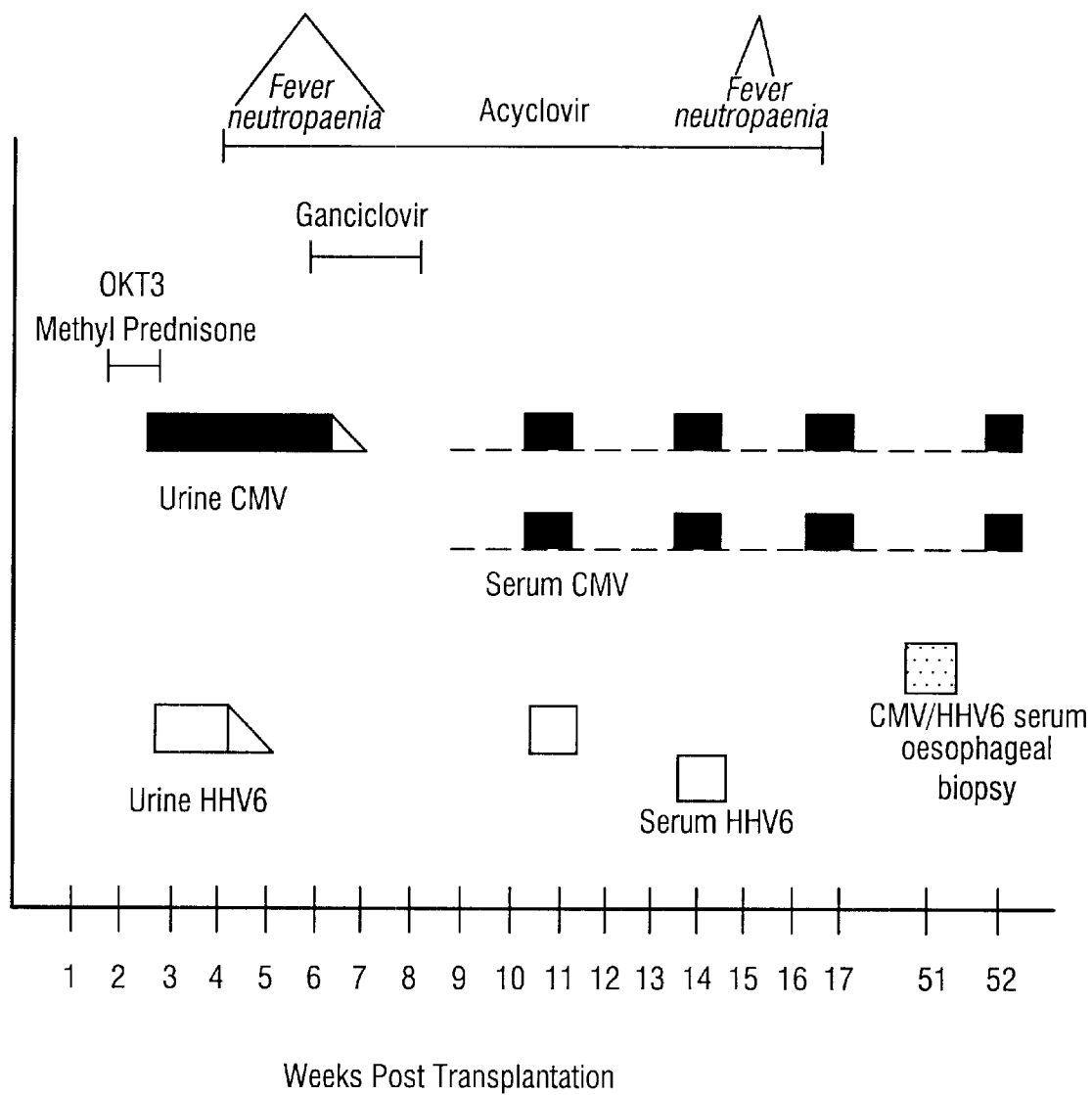
FIG. 2 shows CMV and HHV6 reactivation and febrile disease after OKT3/ATG anti-rejection therapy. Shedding of HHV6 and CMV DNA in urine was detected in the first week after commencement of OKT3 and was associated with fever and neutropaenia. Therapy with ganciclovir but not acyclovir terminated CMV shedding. Urinary shedding of both viruses recommenced several weeks after cessation of ganciclovir, followed by detection of CMV then HHV6 DNA in serum, recrudescence of fever and then oesophagitis. CMV (and HHV6) DNA and CMV early antigens were detected in the oesophageal biopsy.

Shedding of CMV and HHV6 DNA in urine and/or serum, as detected by PCR, was common following transplantation. CMV and HHV6 DNA were shed in the urine of 17 (57%) and 15 (50%) of the 30 patients respectively and in the serum of seven and seven (26%) of 27 tested patients respectively. In most cases, shedding of CMV or HHV6 followed use of one or other biological anti-rejection agents, usually occurring in urine within one week (FIG. 2). DNA from either virus was only detected in the serum of patients after they had received OKT3 or ATG and occurred in 53% of those patients. Biological anti-rejection therapy was followed by urine shedding of CMV DNA in 68%, HHV6 DNA in 55% or either virus in 82%. When both viruses were shed in urine (41%) this was usually seen in the first specimen collected after commencement of OKT3/ATG therapy, making it very difficult to determine which virus reactivated first. All 11 patients who shed both viruses in urine had disease (one with severe and nine with moderate disease).

Prediction of Disease

Logistic regression analysis was used to determine independent predictors of disease (Table 3). Donor-recipient sero-status was actually not quite significant as an independent predictor in this study (OR=7.5; 95% Confidence Level (C.L.)=0.76–74, P=0.085). The use of biological anti-rejection therapy was itself a predictor of disease (OR 5.5; 95% C.L.=1.2–26; P=0.03), but the detection of CMV DNA in either serum or urine was not a useful predictor. Urine or serum HHV6 DNA was, however, significantly associated with disease (OR=27, 95% CL 1.2–578, p=0.035). Detection of both CMV and HHV6 was highly associated with disease and the best independent predictor (OR=99, 95% CL 5.4–1814, p=0.002). All four patients with both HHV6 and CMV in serum had moderate to severe disease, including one patient with biopsy proven invasive (gastrointestinal) CMV disease.

CMV or HHV6 DNA was detected in serum much less frequently than in urine and was a more specific but less sensitive marker of disease (6/7 for CMV and 7/7 for HHV6).

The predictive values of CMV and HHV6 DNA in urine for association with clinically suspected "viral" disease (as defined in this study) were 71% and 93% respectively. The presence of viral DNA in serum had a higher (I positive predictive value for disease: 100% for HHV6 and 86% for CMV.

TABLE 3

Association of CMV and HHV6 with disease in renal transplantation

| Treatment | Univariate Odds Ratio | 95% CL* | P |
|---|---|---|---|
| Donor pos/recipient neg | 7.5 | 0.76–74 | 0.085 |
| OKT3/ATG | 5.5 | 1.2–26 | 0.033 |
| Urine/serum CMV DNA alone | 1.8 | 0.1–35 | 0.69 |
| Urine/serum HHV6 DNA alone | 27 | 1.2–578 | 0.035 |
| +Urine/serum CMV + HHV6 DNA | 99 | 5.4–1814 | 0.002 |

*CL = Confidence Limits
+Enhanced in best fitting multivariate model OR = 168, 95% CL = 9–3019, p = 0.001

Effect of Antivirals

The effect of antivirals on CMV and HHV6 disease was also examined in these patients since 21 patients received acyclovir and seven received ganciclovir. Acyclovir had no apparent effect on the detection of either HHV6 or CMV DNA in urine or serum or on disease. Intravenous ganciclovir terminated shedding of either or both CMV and HHV6 DNA in urine and serum in all cases within one week, although shedding recommenced in six patients after ganciclovir was ceased (FIGS. 1 and 2). In all patients, the viral syndrome responded rapidly to ganciclovir with defervescence and resolution of haematological abnormalities.

HHV6 and CMV Serology

Seven patients seroconverted to HHV6 (or had initially undetectable levels becoming detectable), while 13 had four-fold or greater rises in anti-HHV6 IgG titres and 10 did not show any rise in anti-HHV6 titres. Anti-HHV6 IgM was detectable by three to six weeks in 10 of the 20 patients with significant rises in IgG titres. Two of these 10 patients however did not shed DDNA in either serum or urine.

Six of 10 patients who developed an IgM anti-HHV6 response also had detectable anti-CMV IgM concurrently. In all of these patients, anti-HHV6 IgM became detectable at least one week before anti-CMV IgM developed. Nine of the 10 patients who developed a positive anti-HHV6 IgM response had been treated with OKT3 and the other one received ATG.

Comparison of CMV and HHV6 IgM Response with DNA Detection and Disease

HHV6 DNA was detected in the urine or serum of eight of 10 patients who developed an anti-HHV6 IgM response and in seven patients who did not develop an anti-HHV6 IgM response. HHV6 DNA was always detected 1–2 weeks before the appearance of IgM. CMV DNA was detected in the urine or serum of 12 of 18 patients who developed CMV IgM responses and four of eight who did not develop CMV IgM responses. All patients who developed CMV DNA shedding in urine showed CMV viruria by culture-fluorescence in subsequent samples.

In summary, from a clinician's perspective all 11 patients who had evidence of infection with both viruses had clinical disease; while 4 of 10 with evidence of infection with only one of the viruses had clinical disease, all of which were probably primary infections by the relevant virus.

Discussion

In this prospective study of 30 consecutive patients undergoing renal and simultaneous pancreas/renal transplantation, intensive virological monitoring revealed the presence of CMV and HHV6 DNA in urine and/or serum.

Correlation of the virological data with clinical events demonstrated disease associated with HHV6 alone consisted of fever with raised serum transaminases, indicating hepatitis, but not neutropaenia or other end organ involvement. Disease associated with CMV alone was only observed in one patient and consisted of fever and neutropaenia. The majority of viral disease was associated with shedding of both CMV and HHV6. CMV donor recipient sero-status was not predictive in this study because it was confounded by the effect of anti-rejection therapy in seropositive recipients and the presence of HHV6 disease in seronegative donor-recipient pairs. Nevertheless all five donor-positive, recipient-negative pairs developed viral disease, consistent with the expected high incidence of disease in this setting. The use of anti-rejection therapy was the major factor predisposing to the reactivation of or infection with CMV and HHV6 as more than 80% of CMV and HHV6 shedding and viral disease, occurred in this setting.

The combination of CMV and HHV6 reactivation was associated with disease and the presence of CMV and HHV6 DNA in serum together was the best predictor of severe disease. These findings strongly suggest that active infection with CMV and HHV6 occurred both independently and together, as previously determined by serologic studies, but their combination resulted in high likelihood of disease.

From a clinical perspective, CMV and HHV6 DNA were useful predictors of disease, occurring early in the course of the disease, demonstrating a response to ganciclovir and correlating well with subsequent antibody responses which occurred too late after the onset and were less specific for disease. Total antibody rises were less specific for disease than PCR and HHV6 IgM response usually followed DNA shedding as previously reported. The 23% incidence of seroconversion appeared paradoxical in view of the high rate of acquisition of HHV6 in infancy. This can be explained by the subsequent progressive decline in antibody titre resulting in an increased proportion of apparently seronegative adults.

The present data supports the specificity of plasma or serum CMV DNA as a predictor for CMV disease. Nevertheless, it was a relatively insensitive marker in this study, with a sensitivity of 50% and specificity of 86%. The specificity of serum HHV6 DNA for disease was 100% while a combination of serum HHV6+ClvV DNA predicted 75% of disease episodes.

There have been anecdotal reports of the association of HHV6 and CMV as copathogens in pneumonilis and other disease in transplant patients. In addition, the recently reported association of HHV6, allograft dysfunction and graft versus host disease is also strongly associated with CMV and suggests these viruses may be copathogens in a number of settings. Interestingly, evidence for coincident HIV and HHV6 infection of the retina in predisposing to CMV retinitis has also been recently reported in a post mortem study, although this was not supported by vitreous sampling for CMV and HHV6 DNA.

In conclusion, definition of both the donor and recipient HHV6 as well as CMV status may help determine which patients are at risk of disease after organ transplantation.

Publications referred to above are incorporated herein in their entirety by reference.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

1. Mullis, K. B. (1987) Process for amplifying nucleic acid sequences. U.S. Pat. No. 4,683,202.
2. Mullis, K. B., Erlich, H. A., Arnheim, N., Horn, G. T., Saiki, R. K. and Scharf, S. J. (1987) Process for amplifying, detecting, and/or cloning nucleic acid sequences. U.S. Pat. No. 4,683,195.
3. Mullis, K., Faloona, F., Scharf, S., Saiki, R., Horn, G. and Erlich, H. (1986) Specific enzymatic amplification of DNA in vitro: the polymerase chain reaction. Cold Spr. Harb. Symp. Quant. Biol. 51:263–273.
4. Erlich, H. A., ed. (1989) "PCR Technology. Principles and Applications for DNA Amplification." (Stockton Press, New York).
5. Kwoh, D. Y., Davis, G. R., Whitfield, K. M., Chappelle, H. L., DiMichele, L. J. and Gingeras, T. R. (1989) Transcription-based amplification system and detection of amplified human immunodeficiency virus type 1 with a bead-based sandwich hybridisation format. Proc. Natl. Acad. Sci. USA 86:1173–1177.
6. Malek, L. T., Davey, C., Henderson, G. and Sooknanan, R. (1992) Enhanced nucleic acid amplification process. U.S. Pat. No. 5,130,238.
7. Wu, D. Y. and Wallace, R. B. (1989) The ligation amplification reaction (LAR): amplification of specific DNA sequences using sequential rounds of template-dependent ligation. Genomics 4:560–569.
8. Barany, F., Zebala, J., Nickerson, D., Kaiser, R. J., Jr. and Hood, L. (1996) Thermostable ligase-mediated DNA amplifications system for the detection of genetic disease. U.S. Pat. No. 5,494,810.
9. Birkenmeyer, L. G., Carrino, J. J., Dille, B. J., Hu, H.-Y., Kratochvil, J. D., Laffler, T. G., Marshall, R. L., Rinehardt, L. A. and Solomon, N. A. (1995) Amplification of target nucleic acids using gap filling ligase chain reaction. U.S. Pat. No. 5,427,930.
10. Backman, K. C., Carrino, J. J., Shimer, G. H. and Yocum, R. R. (1996) Ligase chain reaction with endonuclease IV correction and contamination control. U.S. Pat. No. 5,516,663.
11. Gopal M R, Thomson B J, Fox J, Tedder R S, Honess R W. Detection by PCR of HHV6 and EBV DNA in blood and oropharynx of healthy adults and HIV seropositive patients. Lancet 1990;335:1598–99.
12. Lawrence G L, Chee M, Craxton M A, Gompels U A, Honess R W, Barrell B G. Human herpesvirus 6 is closely related to human cytomegalovirus. Virol 1990;64:287–99.
13. Demmler G J, Buffone G J, Schimbor C M, May R. Detection of cytomegalovirus in urine from newborns by using polymerase chain reaction DNA amplification. J Inf Dis 1988;158:1177–84.
14. Ratnamohan V M, Mathijs J M, McKenzie A, Cunningham A L. HCMV-DNA is detected more frequently than infectious virus in blood leucocytes of immunocompromised patients: A direct comparison of culture-immunofluorescence and PCR for detection of HCMV in clinical specimens. J Med Virol 1992;38:252–59.
15. Irving W L, Cunningham A L. Serological diagnosis of infection with human herpes virus type 6. Brit Med J 1990;300:156–58.

What is claimed is:

1. An isolated nucleic acid molecule complementary to and specific for human herpes virus 6 (HHV6) DNA comprising a sequence selected from the group consisting of 5'CTTCTGTTTTAAGTCGTACAGGAGT (SEQ ID NO:1) and 5'ACAAGTTGCCATTTCGGGGAAGTAC (SEQ ID NO:2), wherein the nucleic acid molecule is less than about 50 nucleotides in length.

2. An isolated nucleic acid molecule as claimed in claim 1 in which the nucleic acid molecule is less than about 35 nucleotides in length.

3. An isolated nucleic acid molecule as claimed in claim 1 in which the molecule consists of the sequence 5'CTTCT-GTTTTAAGTCGTACAGGAGT (SEQ ID NO:1)or 5'ACAAGTTGCCATTTCGGGGAAGTAC (SEQ ID NO:2).

* * * * *

SEQUENCE LISTING

<160> NUMBER OF SEQ ID NOS: 8

<210> SEQ ID NO 1
<211> LENGTH: 25
<212> TYPE: DNA
<213> ORGANISM: Human herpesvirus 6

<400> SEQUENCE: 1
cttctgtttt aagtcgtaca ggagt                                              25

<210> SEQ ID NO 2
<211> LENGTH: 25
<212> TYPE: DNA
<213> ORGANISM: Human herpesvirus 6

<400> SEQUENCE: 2
acaagttgcc atttcgggga agtac                                              25

<210> SEQ ID NO 3
<211> LENGTH: 25
<212> TYPE: DNA
<213> ORGANISM: Human herpesvirus 6

<400> SEQUENCE: 3
aagcttgcac aatgccaaaa aacag                                              25

<210> SEQ ID NO 4
<211> LENGTH: 25
<212> TYPE: DNA
<213> ORGANISM: Human herpesvirus 6

<400> SEQUENCE: 4
ctcgagtatg ccgagacccc taatc                                              25

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: PCR primer

<400> SEQUENCE: 5
aactgtctga ctggcaaaaa ctttt                                              25

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: PCR primer

<400> SEQUENCE: 6
ccaagcggcc tctgataacc aagcc                                              25

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: PCR primer

<400> SEQUENCE: 7
cagcaccatc ctcctcttcc tctgg                                              25

```
<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Probe

<400> SEQUENCE: 8
aggctattgt agcctacact ttg                                          23
```